(12) United States Patent
Rick et al.

(10) Patent No.: US 7,669,598 B2
(45) Date of Patent: Mar. 2, 2010

(54) REMOTE CONTROL AND TACTILE FEEDBACK SYSTEM AND METHOD FOR MEDICAL APPARATUS

(75) Inventors: Norman A. Rick, Mt. Horeb, WI (US); Ronald L. Tobia, Sun Prairie, WI (US)

(73) Assignee: Datex-Ohmeda, Inc., Madison, WI (US)

( * ) Notice: Subject to any disclaimer, the term of this patent is extended or adjusted under 35 U.S.C. 154(b) by 1504 days.

(21) Appl. No.: 10/991,685

(22) Filed: Nov. 18, 2004

(65) Prior Publication Data

US 2005/0066969 A1    Mar. 31, 2005

Related U.S. Application Data

(63) Continuation-in-part of application No. 09/924,148, filed on Aug. 7, 2001, now Pat. No. 6,834,647.

(51) Int. Cl.
  *F16K 31/02* (2006.01)
(52) U.S. Cl. .............................. 128/204.21; 128/200.14; 128/200.24; 128/203.12; 128/203.14; 128/204.18; 128/205.24; 128/207.14; 128/207.13; 128/207.16; 128/207.18; 128/204.22; 128/204.23; 128/204.29; 128/903; 128/904; 128/905; 128/920
(58) Field of Classification Search ............ 128/200.14, 128/200.24, 203.12, 203.14, 204.18, 205.24, 128/207.14, 207.15, 207.16, 207.17, 207.18, 128/204.21, 204.22, 204.23, 204.29, 903, 128/904, 905, 920
See application file for complete search history.

(56) References Cited

U.S. PATENT DOCUMENTS 3,256,876 A    6/1966    Elam (Continued)

FOREIGN PATENT DOCUMENTS

JP    11-262492 A    9/1999

(Continued)

OTHER PUBLICATIONS

European Search Report for corresponding European Patent Application No. 07 01 7940, having a completion date of Oct. 26, 2007.

*Primary Examiner*—Patricia M Bianco
*Assistant Examiner*—Nihir Patel
(74) *Attorney, Agent, or Firm*—Andrus, Sceales, Starke & Sawall, LLP

(57) ABSTRACT

A system and method are for monitoring control signals provided to a medical apparatus bases upon tactile feedback from the apparatus. The system and method employ a monitoring signal indicative of a parameter relating to the apparatus or to a condition of a patient associated with the apparatus. The system includes a first feedback device in communication with the apparatus and arranged to provide tactile feedback to a first individual based upon the monitoring signal; a first controller actuatable by the first individual to provide a control signal to the apparatus for carrying a control action in the apparatus; a second feedback device in communication with the apparatus and arranged to provide tactile feedback to a second individual based upon the monitoring signal from the apparatus; and a second controller in communication with the first controller such that the control signal given by the first individual to the first controller is reflected in the second controller and communicated to the second individual. The first feedback device, first controller, second feedback device and second controller are in communication with the apparatus such that the first and second individual can be distant from the apparatus and patient and move about the apparatus and patient to a desired location.

20 Claims, 11 Drawing Sheets

U.S. PATENT DOCUMENTS

| | | |
|---|---|---|
| 3,874,378 A | 4/1975 | Isaacson et al. |
| 3,890,967 A | 6/1975 | Elam et al. |
| 3,973,564 A | 8/1976 | Carden |
| 4,187,845 A | 2/1980 | Dror |
| 4,991,576 A | 2/1991 | Henkin et al. |
| 5,231,981 A | 8/1993 | Schreiber et al. |
| 5,507,280 A | 4/1996 | Henkin et al. |
| 5,537,999 A | 7/1996 | Dearman et al. |
| 5,564,416 A | 10/1996 | Jones |
| 5,628,305 A | 5/1997 | Melker |
| 5,651,361 A | 7/1997 | Dearman et al. |
| 5,694,924 A | 12/1997 | Cewers |
| 5,711,295 A | 1/1998 | Harris, II |
| 5,868,133 A | 2/1999 | DeVries et al. |
| 5,975,078 A | 11/1999 | Pauley |
| 6,036,662 A | 3/2000 | Van Brunt et al. |
| 6,074,213 A | 6/2000 | Hon |
| 6,459,933 B1 | 10/2002 | Lurie et al. |
| 7,247,154 B2 * | 7/2007 | Hickle ........................ 604/500 |
| 2002/0133061 A1 | 9/2002 | Manetta |

FOREIGN PATENT DOCUMENTS

| | | |
|---|---|---|
| WO | 99/62403 | 12/1999 |
| WO | 00/30548 A1 | 6/2000 |
| WO | 00/67827 | 11/2000 |

* cited by examiner

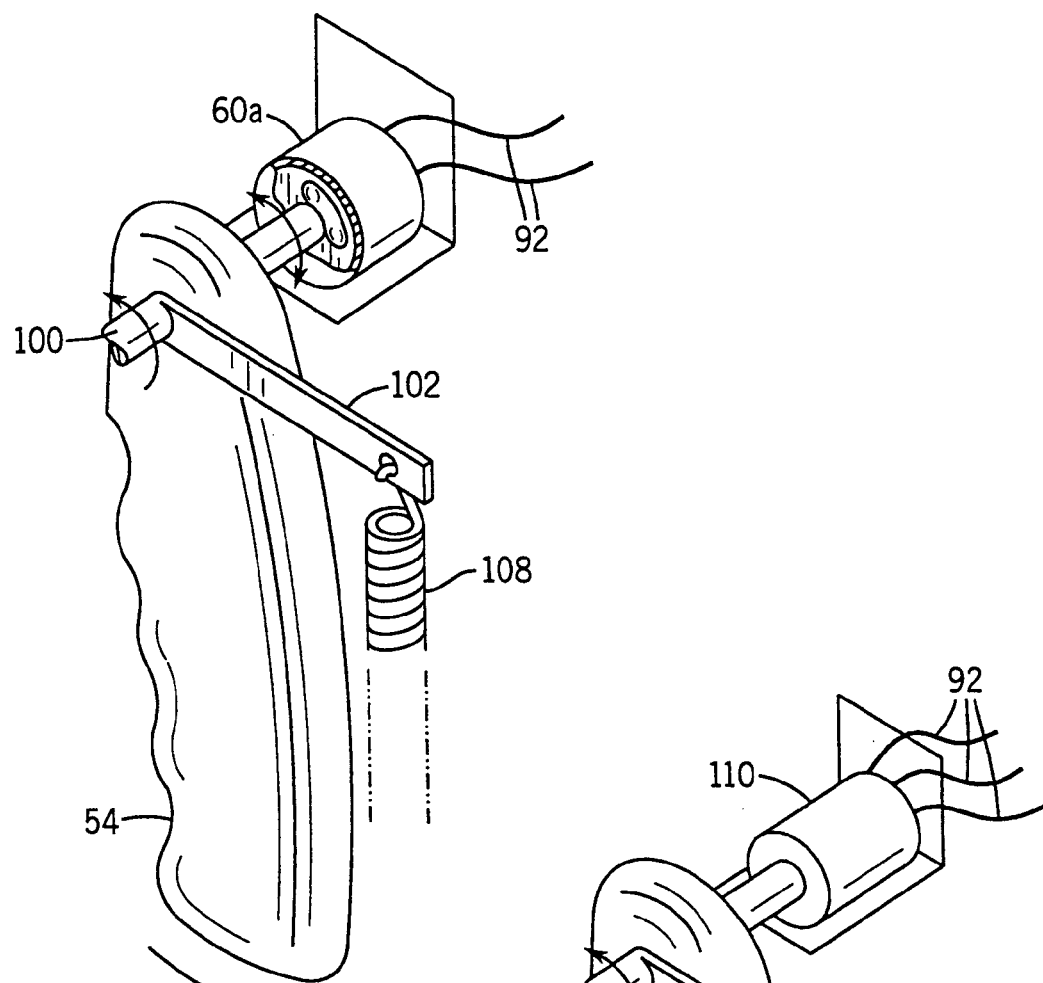
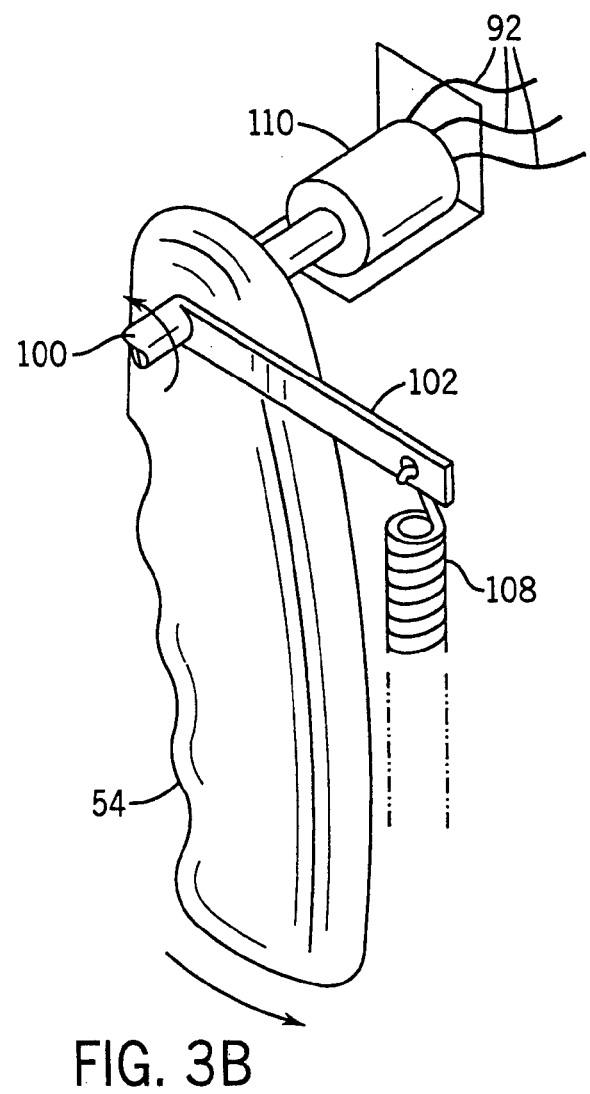
FIG. 3A
FIG. 3B

REMOTE CONTROL AND TACTILE FEEDBACK SYSTEM AND METHOD FOR MEDICAL APPARATUS

CROSS REFERENCE TO RELATED APPLICATION

This application is a continuation-in-part of application Ser. No. 09/924,148, filed Aug. 7, 2001, U.S. Pat. No. 6,834,647.

BACKGROUND OF THE INVENTION

The present invention relates to a system providing remote control to medical apparatus, such as a respiratory ventilator for a patient. The system also provides a tactile expression of a parameter relating to a patient or a medical apparatus to a user of the apparatus. For example, the system may provide a tactile indication of a breathing characteristic of a patient connected to a ventilator to a clinician using the system.

In one aspect of the system of the present invention, a manual member has a handle with a moveable, trigger-like member. The handle and trigger are gripped by the user. When the trigger is squeezed by the user, a signal generator is operated to provide a control signal, through a cable or other suitable means, to the ventilator for use in controlling the apparatus. For example, the control signal may be used to control the supply of breathing gases to a patient.

Medical equipment, such as a ventilator, includes sensors providing signals corresponding to various parameters relating to a patient or the apparatus. In another aspect of the invention, a signal corresponding to a parameter, for example patient airway pressure, may be returned, or fed back, from the apparatus to a manual member having a trigger. The feedback signal drives an actuator for the trigger to cause the trigger to exert a force on the fingers of the user that indicates to the user the breathing characteristic of the patient.

In a preferred embodiment of the system, a single manual member is used for both control and feedback purposes.

Respiratory ventilators provide breathing gases to a patient via a breathing circuit. The breathing circuit typically has an inspiratory limb and an expiratory limb. One end of each of the inspiratory and expiratory limbs are connected to the ventilator. The other ends are connected to a Y-connector and through a patient limb to the patient. Pneumatic elements in the ventilator periodically provide breathing gases to the patient through the inspiratory limb during inhalations. On expirations, the breathing gases are discharged from the lungs of the patient into the expiration limb. Controls in the ventilator establish parameters, such as breaths/minute, tidal volume, maximum pressures, etc. that characterize the ventilation provided to the patient by the ventilator.

A patient may also be manually ventilated by means of a flexible container or "bag" provided on the ventilator. The bag is filled with breathing gases and manually squeezed by a clinician to provide breathing gases to the patient. Use of the bag, or "bagging the patient," is often required or preferred by clinicians as it enables the clinician to physically control the delivery of breathing gases to the patient. Equally important, the feel of the bag as it is manipulated by the clinician enables the clinician to sense conditions in the lungs and respiration of the patient. In the hands of a skilled clinician, subtle characteristics and/or changes in the lungs and respiration can be sensed. It is difficult or impossible to obtain this type of feedback information when mechanical ventilating apparatus provides the breathing gases.

For the foregoing reasons, patients are often bagged during surgical procedures when anesthesia is induced in the patient by entraining an anesthetic in the breathing gases. Another environment in which patients are often bagged is in an intensive care unit.

However, if bagging is carried out for a long time, it becomes fatiguing to the clinician lessening both the fineness of the control of breathing gas supply and the sensing of lung or other respiratory conditions affecting the subject.

Also, the bag is usually positioned at a fixed location on the ventilator. This restricts the degree to which the clinician, when bagging a patient, can move about the patient, for example, to observe a surgical patient positioned in a manner appropriate to the surgery to be performed. The same is true when the pneumatic elements of the ventilator, rather than the bag, are providing the breathing gases to the patient since the controls necessary to operate the pneumatic elements are placed at a fixed location on the ventilator.

It is further recognized that current medical practice often requires several years of hands-on experience with a particular medical apparatus for a caregiver to become educated as to how to appropriately operate the apparatus to treat a wide variety of patient ailments. For example, the manual ventilation procedures described above are useful to treat many different respiratory ailments. Current practice unfortunately requires the caregiver to acquire several years of experience manually ventilating patients having different respiratory ailments in order to develop a sufficient understanding as to how to operate the device. Additionally, unique lung diseases may call for unusual practice that is not easily simulated in the field or classroom.

As such, it is desirable to provide a system and method that decreases the time necessary to train clinicians to operate medical apparatus to treat a wide variety of medical ailments. It is desirable to provide a system and method that is easy to use in either a classroom or hospital setting, and that allows the experienced and inexperienced clinician to move about a patient and medical apparatus while operating the apparatus. It is further desirable to provide a system and method that is easily adjusted to provide tactile feedback representative of a wide variety of patient ailments and symptoms.

SUMMARY OF THE PRESENT INVENTION

It is, therefore, an object of the present invention to provide a system that enables a clinician, or other user to remotely control medical apparatus, such as a ventilator. The invention may also remotely provide a tactile sensory indication of a parameter, such as a respiratory parameter of a patient connected to a medical apparatus.

The fact that the system is remote, allows the clinician, or other user for the system to move with respect to the apparatus to which the system is connected and with respect to a patient being treated by the apparatus, thereby to improve the effectiveness of care provided to the patient.

In applications involving a respiratory parameter, the system of the present invention provides a control operation and feedback sensation resembling that experienced by a clinician when manually feeling the bag. This enables the clinician to sense and control conditions in the patient in a highly effective manner. However, the system of the present invention avoids the fatigue incurred with manually bagging the patient. The sensing and control provided by the present invention can be enhanced by adjusting the sensitivity and linearity between the control and feedback signals and the resulting control action and tactile sensation generation. This enables an optimal relationship to be established between user input and ventilation delivery for a particular patient.

While the foregoing has described the present invention in connection with sensing ventilation parameters, it may also be used to provide a tactile feedback of other parameters. For example, the system may be used to provide a tactile indication of the cardiac properties, such as blood pressure or pulse rate.

Briefly, the present invention provides a remote feedback system for providing a tactile expression of a characteristic of a parameter of an apparatus to which the system is connected. The apparatus provides a feedback signal indicative of the parameter. The system typically includes a member having a moveable trigger. An electromechanical, or fluidic force applying actuator, such as a linear motor, is coupled to the trigger. The feedback signal is provided to the actuator by a communication means, such as a cable or telemetry link. When the member and trigger are gripped by the user, the forces exerted on the fingers of the user by the trigger, as the trigger is driven by the actuator, are an indication of a characteristic of the parameter of the apparatus.

By providing the system with a potentiometer, or other signal generator, operated by the trigger, the system can also provide a signal to control the operation of ventilator apparatus via the communication means.

Another embodiment of the present invention provides a unique system that facilitates monitoring the use of medical apparatus based upon tactile feedback. In one example, the system employs a monitoring signal indicative of a parameter relating to the apparatus or to a condition of a patient associated with the apparatus. The system includes (1) a first feedback device in communication with the apparatus and arranged to provide tactile feedback to a first individual based upon the monitoring signal; (2) a first controller actuatable by the first individual to provide a control signal to the apparatus for carrying out a control action in the apparatus; (3) a second feedback device in communication with the apparatus and arranged to provide tactile feedback to a second individual based upon the monitoring signal from the apparatus; and (4) a second controller in communication with the first controller such that the control signal given by the first individual to the first controller is communicated to the second individual. The control signal may be communicated to the second individual through, for example, audio signals, visual signals or in the form of tactile feedback. The first and second feedback devices and first and second controllers are in communication with the apparatus such that the first and second individuals can be distant from the apparatus and patient and move about the apparatus and patient to a desired location.

In one example of the invention, an experienced caregiver operates the first manual control and tactile feedback member, while a student or inexperienced caregiver operates the second manual control and tactile feedback member. The control actions provided by the experienced caregiver with the first manual member are communicated to the student, thereby providing the student with an example of how to control the medical apparatus depending upon the particular feedback presented.

The above described embodiment can be employed in a teaching setting to significantly reduce the required training time, as compared to the several years of incidental experience required by known teaching methods and systems. In addition, less common lung diseases can be part of the condensed training via acoustic mapping and unique feedback. For example, the link between the first and second controllers can be established in the operating room and the interactive feedback established between the experienced caregiver, an inexperienced caregiver or student, and a real patient or test lung. A response signature for a particular ailment can be mapped according to specific lung diseases (for example, several types of asthma, cystic fibrosis, etc.). This will provide a unique digital signal to be applied to the feedback devices. The experienced caregiver can then select a particular disease and activate the first controller and feedback device. Feedback from the unique qualities of the selected illness is then replicated in the second feedback device sensed by the student. In addition, the student can monitor, observe, or sense control signals provided by the experienced caregiver. This advantageously trains the student in a relatively short time, compared to actual practice, and provides significant advantages over known systems and methods.

In another embodiment, the system and method allow the experienced caregiver to monitor the control signals provided by an inexperienced caregiver to the ventilator. This arrangement allows for real-time critique of the student's understanding and ability to control the medical apparatus.

Various other features, objects, and advantages of the invention will be made apparent from the following detailed description and the drawings.

BRIEF DESCRIPTION OF THE DRAWING

The invention will be further understood from the following detailed description taken in conjunction with the drawings.

In the drawings;

FIG. 3A shows a modification of the manual member having elements for remotely controlling the apparatus to which the manual member is connected;

FIG. 3B shows a further embodiment of a manual member;

DETAILED DESCRIPTION OF THE PREFERRED EMBODIMENT

Figure 1:
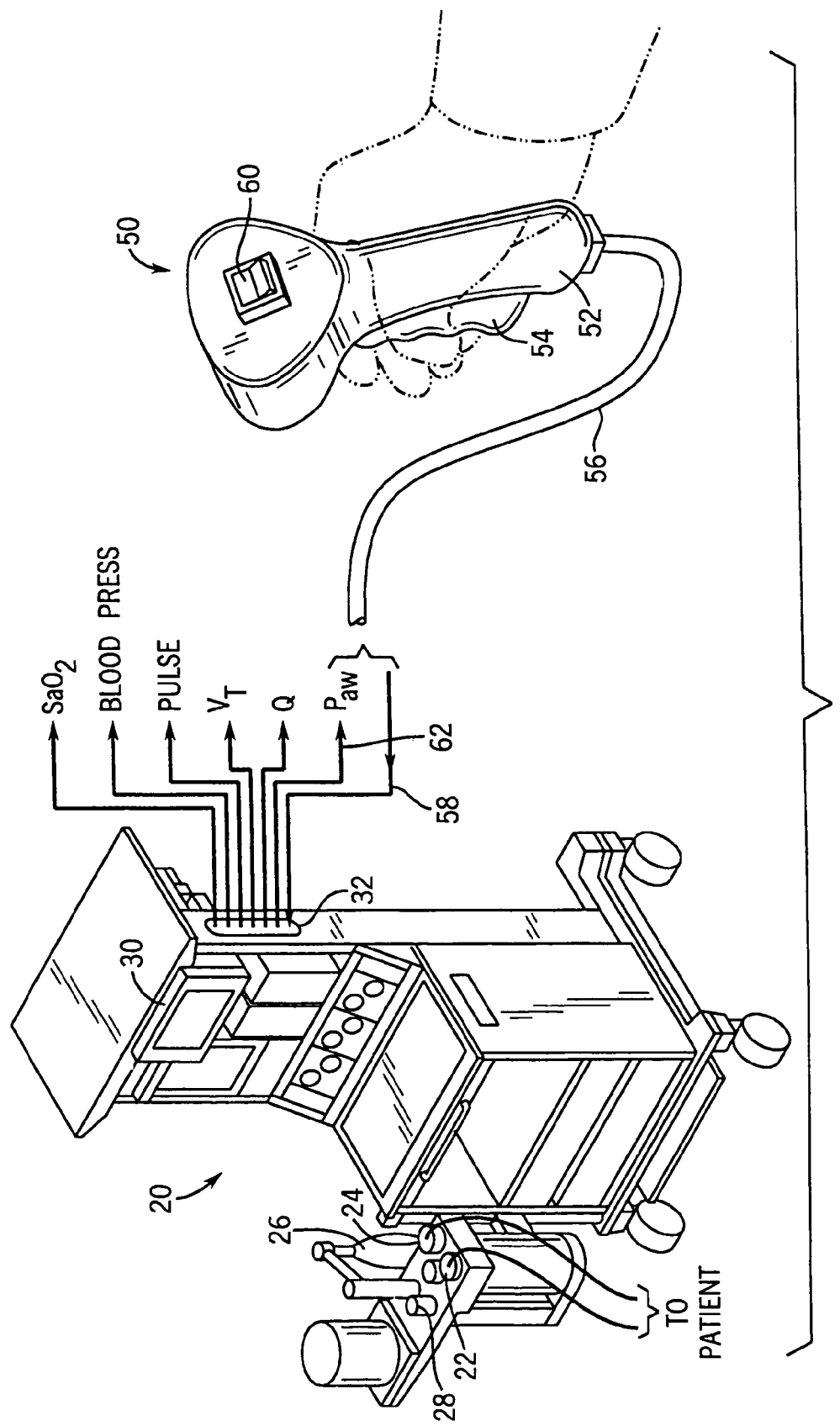
FIG. 1 shows a basic embodiment of the remote control and tactile feedback system of the present invention in use with medical apparatus comprising a ventilator.

Medical apparatus suitable for use with the system of the present invention is shown in FIG. 1 as ventilator 20 incorporated in an anesthesia machine. Ventilator 20 has connectors 22 and 24 suitable for connection to the inspiratory and expiratory limbs of a breathing circuit leading to a patient, as diagrammatically shown in FIG. 1. Ventilator 20 provides breathing gases to the patient in the inspiratory limb of the breathing circuit and receives gases expired by the patient in the expiratory limb.

Ventilator 20 is provided with bag 26 for manually bagging the patient. Switch 28 is operated to allow bag 26 to provide breathing gases to the patient.

Ventilator 20 receives inputs from sensors associated with the patient and/or ventilator 20. The data contained in these inputs may be displayed on patient monitor 30. Data relating to the sensed parameters is also provided to terminal 32. Typical data outputs are shown as patient airway pressure $P_{aw}$, tidal volume $V_T$, breathing gas flow rate Q, pulse rate, blood pressure, and arterial blood oxygen saturation $SaO_2$ parameters.

FIG. 1 also shows member 50 of the remote control and tactile feedback system of the present invention. As shown generally in FIG. 1, member 50 includes grip or handle 52 suitable for received in the hand of a clinician or other user. Trigger 54 is mounted in handle 52 so that the fingers of the user may extend around the exposed edge of the trigger. Trigger 54 pivots with respect to handle 52. Member 50 may be coupled to an apparatus, such as ventilator 20, by cable 56.

Member 50 may be provided with a switch 60 connected, via conductors in cable 56, to apparatus 20 to remotely control apparatus 20 as indicated diagrammatically at 58 in FIG. 1. Actuation of switch 60 may carry out a desired operation of the ventilator. For example, repetitive actuation of switch 60 will cause the ventilator to provide a given quantity of breathing gases to the patient each time the switch is actuated.

In a preferred embodiment of the invention, described in detail, below, a signal generator is connected to trigger 54 and movement of the trigger by the fingers of the operator provides a control signal to remotely control the ventilator. The signal generator may, for example, comprise a switch, a potentiometer or a rheostat. Switch 60 may then comprise an on-off switch to cause ventilator 20 to be operated in the ordinary manner or under the control of member 50.

Cable 56 also contains a conductor providing, or feeding back, a signal corresponding to one of the parameters outputted by apparatus 20. In the example shown in FIG. 1, patient airway pressure $P_{aw}$ is fed back, as diagrammatically indicated at 62. The signal corresponding to parameter 62 is provided to a tactile feedback generator or actuator in member 50 for trigger 54 that applies corresponding force to the fingers of the user holding member 50. This provides a tactile indication or impression to the operator of the parameter that is fed back from the medical apparatus.

With member 50 coupled to apparatus 20 via cable 56, it will be appreciated, that the clinician or other user can move about the apparatus and patient to a desired location, while at the same time maintaining control over the operation of ventilator 20 and receiving the tactile feedback corresponding to a desired parameter.

Figure 2:
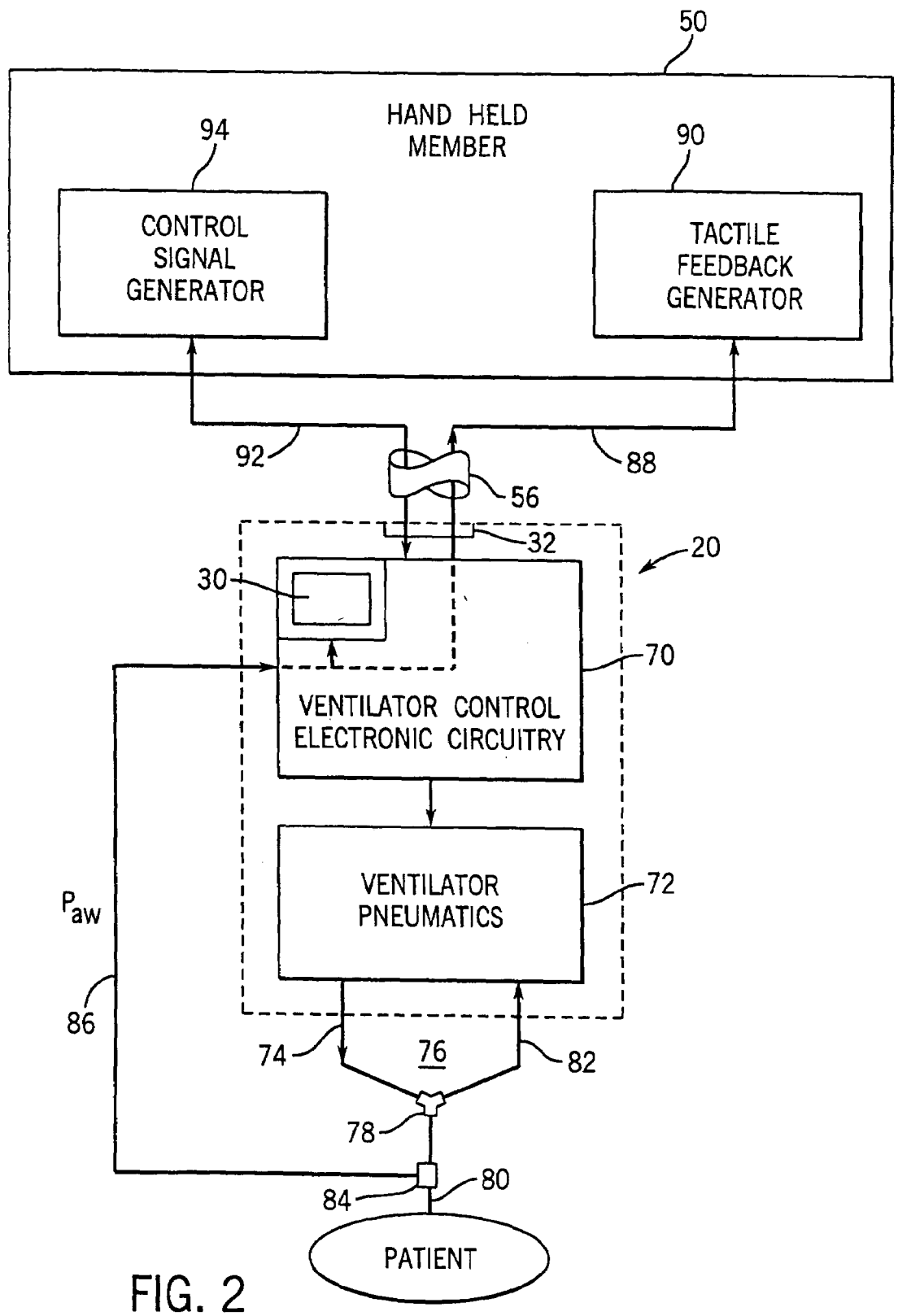
FIG. 2 is a schematic diagram of the system of the present invention in conjunction with ventilator apparatus.

FIG. 2 shows a schematic diagram of member 50 in conjunction with an apparatus 20 comprising a ventilator for a patient. Ventilator 20 includes electronic control circuitry 70 that operates ventilator pneumatic circuitry 72. Pneumatic circuitry 72 comprises a source of pressurized gas that provides breathing gases in inspiratory limb 74 of a patient breathing circuit 76. Pneumatic circuitry 72 may provide breathing gases directly to the lungs of the patient, as in a typical critical care application. Or, a driving gas provided by pneumatic circuitry 72 may compress a bellows containing the breathing gases which, in turn, supplies the gases to the patient, as in a typical anesthesia application. The breathing gases pass through Y-connector 78 to patient limb 80 for supply to the patient. The breathing gases are returned to ventilator 20 in expiratory limb 82. In the embodiment shown in FIG. 2, pressure sensor 84 provides an airway pressure $P_{aw}$ signal in conductor 86 to ventilator control electronic circuitry 70. The signal in conductor 86 is proportional to the pressure in patient limb 80 leading to the lungs of the patient. Ventilator control electronic circuitry 70 may include monitor 30 that provides a numeric or graphic display of patient airway pressure $P_{aw}$, as well as other patient or apparatus parameters. The signal from airway pressure sensor 84 is also provided in conductor 88 of cable 56 to member 50. The signal in conductor 88 is supplied to tactile feedback generator 90 to operate trigger 54 in a manner to provide a tactile expression of the magnitude of the patient airway pressure $P_{aw}$ to the fingers of the user engaging trigger 54.

Cable 56 also includes conductor 92 connected to control signal generator 94 for use in controlling ventilator 20. As noted above, control signal generator may comprise switch 60 or a signal generator, such as a potentiometer, operable by trigger 54.

Figure 3:
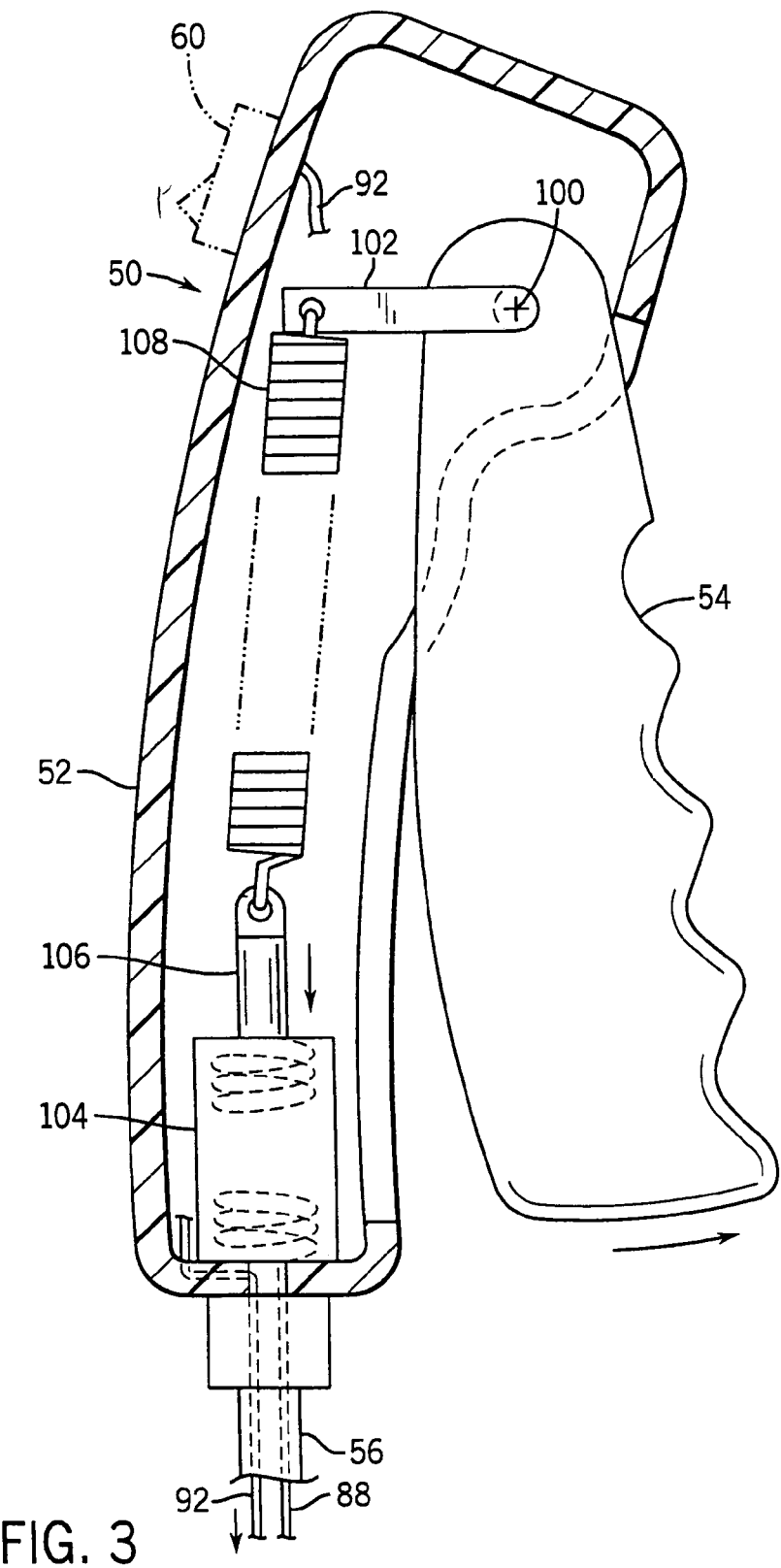
FIG. 3 shows one embodiment of a manual member of the system having elements providing a mechanically generated tactile feedback sensation to a user.

FIG. 3 shows one construction for member 50. Member 50 includes switch 60 connected to conductor 92 for controlling ventilator 20 or for turning the system on or off. Trigger 54 is affixed to shaft 100 that is journaled in handle 52. Arm 102 extends from shaft 100. Electromagnetic actuator 104 comprises armature 106 extending from a coil of wire in the actuator. The coil surrounds armature 106 and is connected to conductor 88. The exposed end of armature 106 is connected via spring 108 to arm 102 to form the tactile feedback generator 90 shown in FIG. 2

When actuator 104 is energized by the feedback signal from apparatus 20 in conductor 88, armature 106 is drawn into the coil of wire in the actuator 104 in the well known manner of a solenoid, as shown by the arrow in FIG. 3. This movement exerts a force on the end of arm 102 tending to cause trigger 54 to rotate in the clockwise direction also as shown in FIG. 3. When member 50 is held in the hand of a user, with handle 22 in the palm of the user's hand and the fingers of the operator extending around the trigger 24, as shown in FIG. 1, the force urging the clockwise rotation of trigger 54 will be felt as a tactile sensation on the inner surfaces of the fingers of the user. The magnitude of the sensation will be proportional to the degree of actuation of the coil of actuator 104 and hence the magnitude of the signal in conductor 88 and the sensed parameter. The experience to the clinician or other user will thus resemble that of manipulating a ventilator bag so that the user has a "feel" of the ventilation being provided to a patient.

As noted above, switch 60 in member 50 may be used to render member 50 operative or as inoperative. Or, switch 60 may be used to operate apparatus 20, for example, to deliver a preset volume of breathing gas to the patient connected to the ventilator over a given period of time. Or, switch 60 can be used to select the parameter that is to be indicated in a tactile manner. For example, the switch may be used to operate circuitry located in member 50 or apparatus 20 to select tidal volume $V_T$ as the monitored parameter for which a tactile expression is provided. Switch 60 may be of any type suitable for the desired purpose, such as a thumbwheel switch, a sliding switch, or a rotary switch.

In another embodiment of member 50, the control element may be mounted in member 50 in a manner such that it can operated when the trigger 54 is moved into member 52 when the user squeezes trigger 54. For this purpose, a rotary switch, such as switch 60a, may be mounted on shaft 100, as shown in FIG. 3A. When trigger 54 is squeezed by the hand of the user, the trigger is moved in the counter clockwise direction shown in FIG. 3A, to operate the switch.

FIG. 3B shows a further modification of member 20 in which the wiper of potentiometer 110 is coupled to shaft 100. Potentiometer 110 provides a variable magnitude signal in conductors 92 that is proportional to the movement of trigger 54. This enables member 50 to provide a variable control action in apparatus 20.

In the operation of member 50 shown in FIG. 3B, member 50 is placed, as described above, in the hand of the user with the handle 52 resting in the palm and the fingers extending around trigger 54. The user squeezes trigger 54. This rotates trigger 54 in the counter clockwise direction, when the trigger is viewed as in FIG. 3B. It also rotates shaft 100, and the wiper of potentiometer 110 to provide a signal in conductors 92 to the ventilator control circuitry 70 via cable 56. The magnitude of the signal provided to circuitry 70 is proportional to the rotary movement or displacement of trigger 54. Control circuitry 70 operates ventilator pneumatic circuitry 72 to provide a flow of breathing gases from ventilator 20 into inspiratory limb 74 to the patient.

Pressure sensor 84 provides a signal in conductor 86 corresponding to the airway pressure $P_{aw}$ in patient limb 80 resulting from the breathing gas flow. This signal is provided via cable 56 and conductor 88 to tactile feedback generator 90, such as electromagnetic actuator 104, in member 50. In the manner described above, this operates actuator 104 to urge trigger 54 in the clockwise direction of rotation when viewed as in FIG. 1. A force will be felt by the fingers of the user engaged with the trigger 54. The greater the patient airway pressure $P_{aw}$, the greater will be the force felt by the user. The magnitude of the tactile sensation incurred by the user thus provides a feedback indication of the magnitude of the patient airway pressure $P_{aw}$ in the manner of a ventilator bag.

To terminate the inspiratory phase of the respiratory cycle, the user releases trigger 54, allowing it to rotate in the counterclockwise direction when viewed as in FIG. 1. This reduces the magnitude of the signal in conductors 92 to ventilator control electronic circuitry 70 and causes ventilator pneumatic circuitry 72 to cease or reduce supplying breathing gases to the patient. This allows the expiratory phase of the respiratory cycle to commence. During the expiratory phase, airway pressures of the patient will fall. This will reduce the magnitude of the signal in conductor 88 to tactile feedback generator 90. This will correspondingly reduce the force applied to trigger 54 by actuator 104 so that the user has a tactile sense that the airway pressure of the patient has decreased. If desired, trigger 54 may be only partially released so as to provide a positive end expiratory pressure (PEEP) or other desired ventilation protocol in the lungs of the patient.

It will be appreciated from the foregoing explanation, that member 50 shown in FIG. 3B thus operates in a manner analogous to the conventional bag provided on a ventilator. That is, by squeezing trigger 54, a clinician can deliver breathing gases to the patient. This resembles manually squeezing the ventilator bag. Tactile feedback generator 90 provides a resistance or a countering force on trigger 54 that corresponds to the resistance and characteristics of the breathing bag felt by the clinician when manipulating the bag.

In a preferred embodiment of the invention, the system of the present invention may be arranged, by appropriate elements in member 50 or apparatus 20 to establish the flow rate of the breathing gases to the patient proportional to the amount of rotation or angular displacement of trigger 54. This may be accomplished by linear amplification components in control generator 94, ventilator control electronic circuitry 70 and/or ventilator pneumatics 72. This approach provides an easy way for the clinician to establish both the flow rate and the volume of breathing gases delivered to the patient. The delivered volume is the amount of displacement, i.e., flow rate, multiplied by the time during which the flow rate occurs. As the patient airway pressure and tactile feedback increases during inspiration, the clinician will have to increasingly apply more force to trigger 54 in order to maintain a given breathing gas flow.

Alternately, the breathing gas flow rate may be made proportional to the rate of change of displacement of trigger 54. In this approach, the faster trigger 54 is moved, the greater the breathing gas flow rate to the patient. In order to maintain a breathing gas flow to the patient, the trigger must continue to be moved. This embodiment is directly analogous to the conventional ventilator bag. That is, in order to get a continuous flow of breathing gases from the bag to the patient, the clinician must continually squeeze the bag. If the clinician stops squeezing the bag, the flow of breathing gases stops. And further in the manner of a bag, as the patient airway and tactile feedback increases as a result of breathing gas flow to the lungs of the patient, the clinician will have to squeeze trigger 54 harder in order to maintain a given flow of breathing gases to the patient. The action also resembles that of a bag.

To obtain this mode of operation, a differentiator, or time-derivative, component may be used in connection with the signal in conductor 92. An operational amplifier having a capacitor in the input for conductor 92 may be employed.

While the system of the present invention has been described as using control signal generator 90 to control the flow or volume of breathing gases delivered to the patient, it will be appreciated that it may be used to control the pressure of the breathing gases if this mode of ventilation is desired.

By appropriate circuitry/software in member 50 or in ventilator control circuitry 70, the sensitivity of the control action provided by control signal generator 94, such a potentiometer 110, and the feedback action provided by tactile feedback generator 90 can be adjusted. Adjustable gain amplifiers may be used for this purpose. This facilitates the ventilation of patients having differing physiologies or anatomies, for example, a patient with stiff, non-compliant lungs, or a pediatric patient having very small lung volume. The sensitivity of the control action carried out responsive to the signal in conductors 92 from control signal generator 94 can be different from the sensitivity of the tactile feedback provided by tactile feedback generator 90 to trigger 54. For example, when the patient is an infant it may be desirable to have a low sensitivity for control signal generator 94 so that a large input signal to control circuitry 70 provides a relatively small amount of ventilation commensurate with the small lungs of the infant. At the same time, a high sensitivity is provided in tactile feedback generator 90 so that relatively low airway pressure produces a relatively large tactile feedback response. For an adult patient, control signal 90 may have a high sensitivity to reduce the effort required by the user to move the relatively large amount of breathing gases needed for adult patients. The ability to adjust the sensitivity of the tactile feedback generator and the control signal generator enables an optimal user input to ventilation delivery relationship for a particular patient to be established.

Also, by appropriate circuitry/software, the sensitivity of either or both of control and feedback action can be made linear or non-linear, or a combination of the two, over the operating range of the system. Thus, it may be desirable to have the tactile feedback sensation provided to the user increase as a function of patient airway pressure to provide greater sensitivity at higher pressures.

While FIG. 3 shows the use of a linear actuator for actuator 104, it will be appreciated that a rotary actuator, such as an electric motor having a torque arm on the output shaft could also be used to provide the desired tactile sensory indication.

Figure 4:
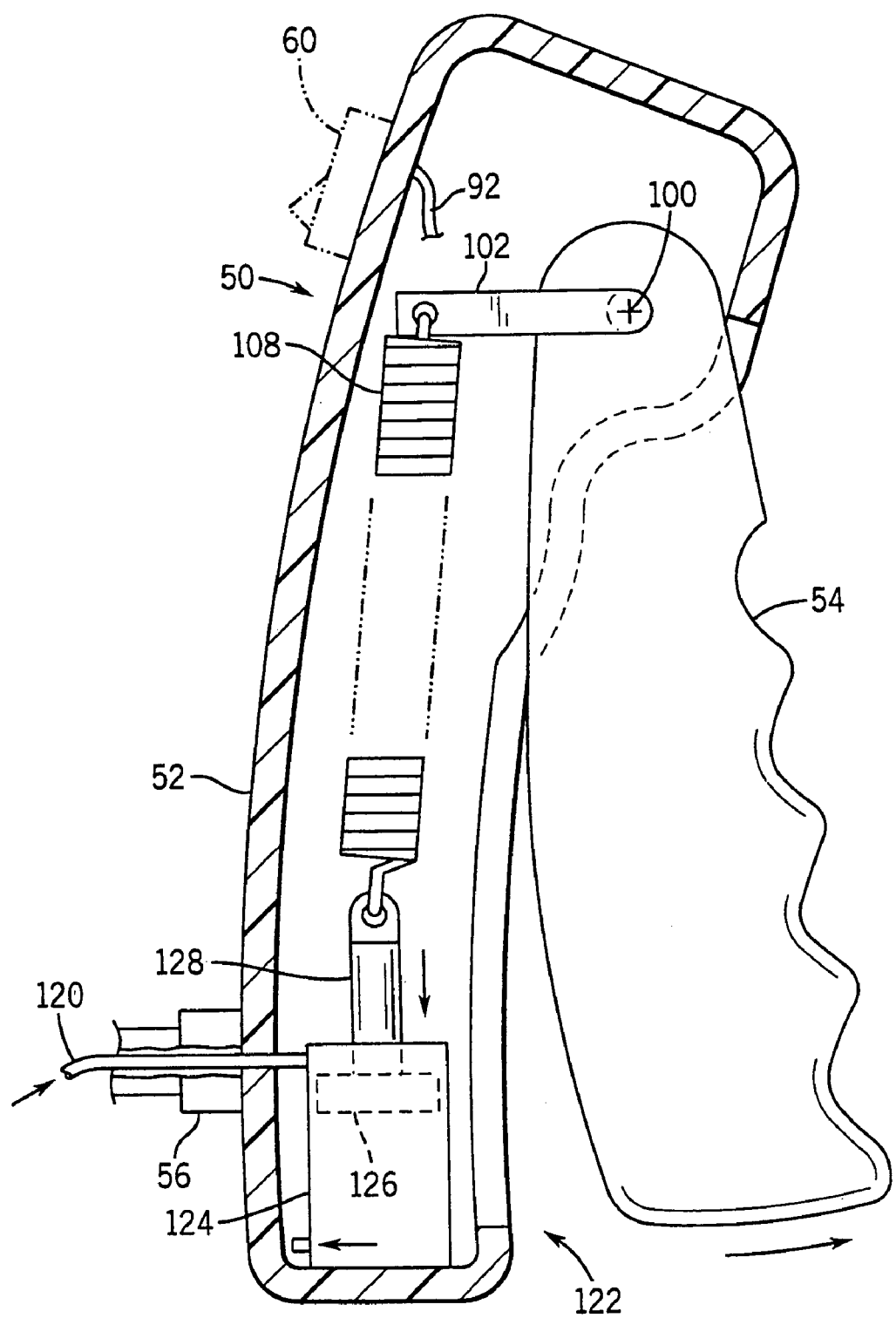
FIG. 4 shows a manual member having a fluid operated means for generating a tactile indication of a parameter.
Figure 9:
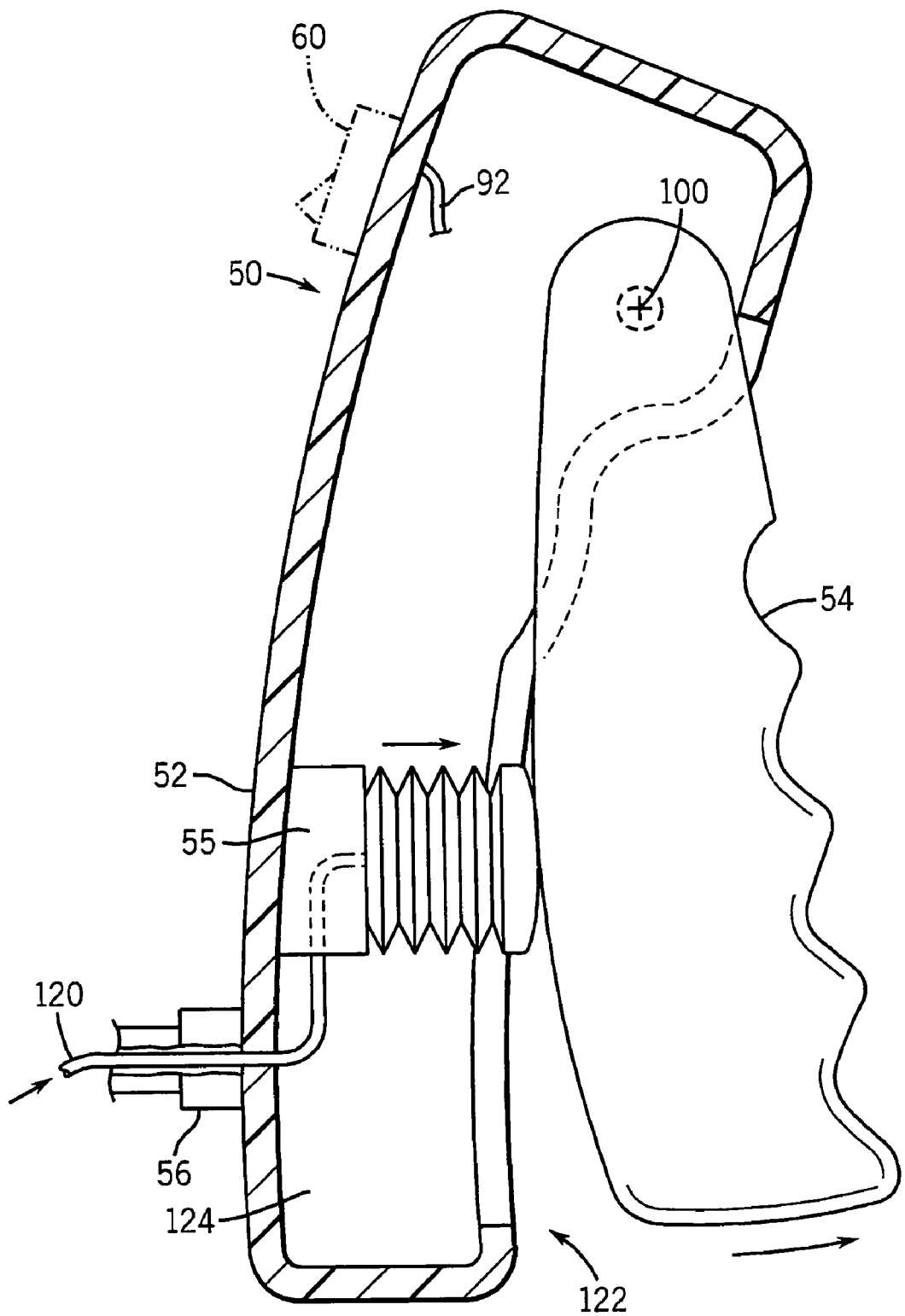
FIG. 9 shows a manual member having a fluid operated means for generating a tactile indication of a parameter.

Also, while FIGS. 3, 3A, and 3B show use of an electromagnetic actuator 104, 106 as tactile feedback generator 90 it will be appreciated that other devices can be used, if desired. FIG. 4 shows the use of an actuator employing a fluid, such as a gas or liquid. For this purpose, cable 56 includes a tube 120 for conveying the fluid to a fluid operated actuator 122 such as an cylinder 124 having piston 126 connected to piston rod 128. Piston rod 126 is connected to spring 108 in the same manner as actuator 106 shown in FIG. 3. Tube 120 receives a pressurized fluid, such as a gas, from ventilator 20 to operate actuator 122. The pressure of the fluid as supplied is proportional to the magnitude of the monitored parameter. Or, as shown in FIG. 9, an expandable bladder 55 that abuts trigger 54 may be used as a tactile feedback generator. Control signal generator 94 may also be a fluidic device, if desired.

FIGS. 1-3 shows the use of cable 56 to provide and receive signals to and from apparatus 20. The electrical signals may be analog, as generally described above. Or, the signals may be digital in which case tactile feedback generator 90 may be a digital stepper motor and control signal generator 94 may be a digital rotary transducer.

The necessary signals to and from member 20 may also be provided optically, in which case cable 56 will include one or more optical fibers. Photo-electric devices in member 50 and ventilator control circuit 70 provide the conversion between electrical and optical signals. Or, an optical link may use invisible light, such as infrared, to provide the necessary communication in which case cable 56 may be eliminated. Infrared sensors and receivers may be utilized in such an embodiment.

Still further, member 50 maybe coupled to apparatus 20 by a radio communications link, such as a telemetry link.

Figure 5:
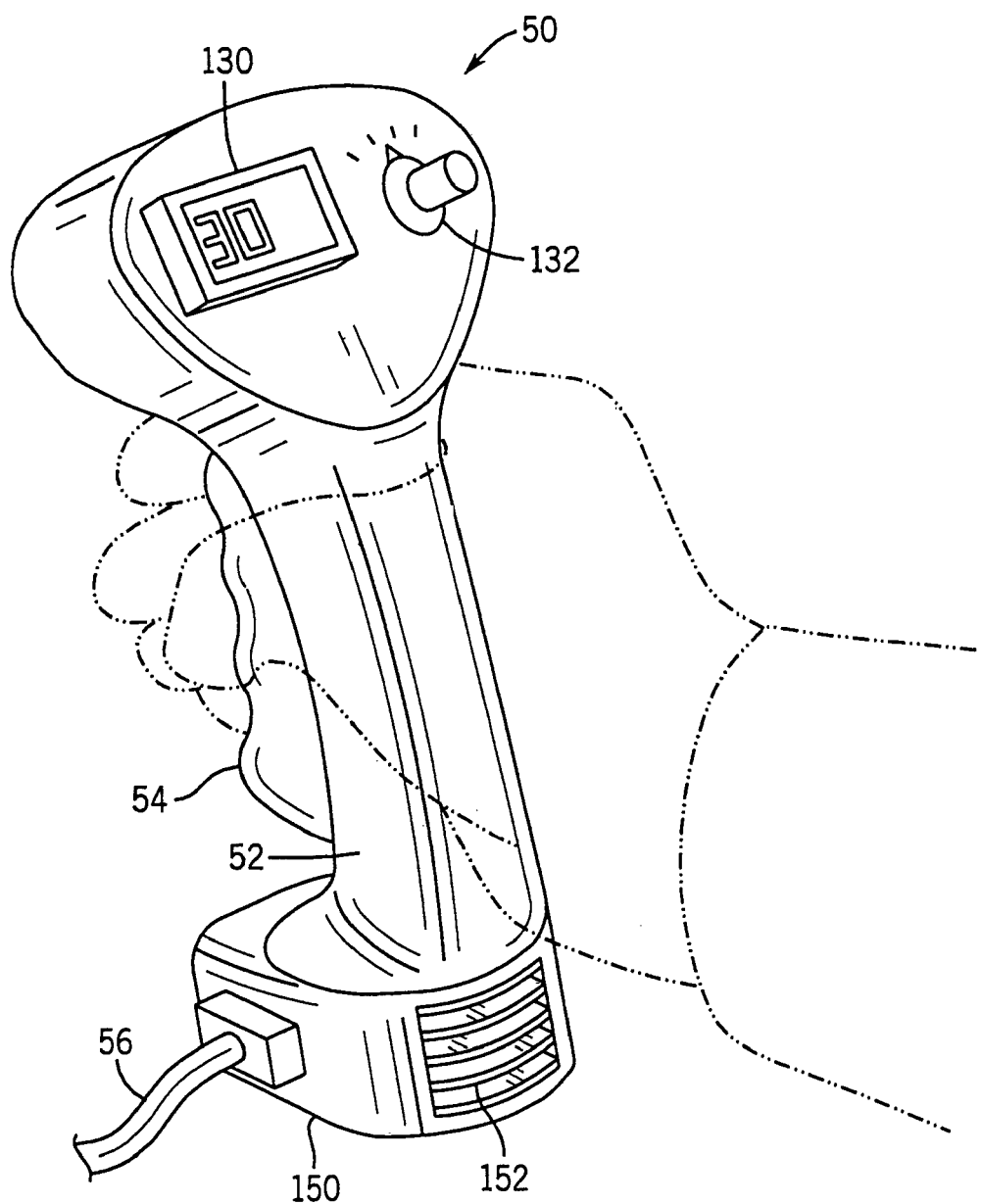
FIG. 5 shows a modification of the manual member of the system of the present invention to include a display and a base.

FIG. 5 shows an embodiment of the invention in which member 50 has display 130. Display 130 may provide a visually perceptible indication of a fedback parameter or of a control action being carried out by apparatus 20. For example, display 130 may show the magnitude of the patient airway pressure $P_{aw}$ fed back to member 50 in conductor 88. Or, display 130 may be coupled to monitor 30 in apparatus 20 to provide graphic or alpha-numeric indication of other information. Rotary switch 132 can be used to select the information to be shown in display 130 and/or to carry out certain settings in apparatus 20.

While the system of the present invention has been described above in connection with a respiratory parameter, such as patient airway pressure $P_{aw}$, other physiological parameters may be indicated in a tactile manner by the system of the present invention. For example, a signal corresponding to the heart rate or pulse of the patient may be provided in conductor 88 to tactile feedback generator 90. Such a signal comprises a series of electrical pulses. The signal will cause tactile feedback generator 90 to provide corresponding force pulsations on trigger 54 and tactile indications to the user of the system of the present invention. The sensation would be somewhat the same as feeling the pulse of a patient at his/her wrist.

It is also possible to provide tactile indications of a plurality of parameters. For example, a tactile feedback of heart rate comprised of a series of pulsations spaced in time can be superimposed on a tactile feedback of patient airway pressure.

Member 50 may be provided with a base 150, as shown in FIG. 5. The base enables member 50 to stand when placed on a flat surface. The base preferably extends beyond trigger 54 to avoid inadvertent operation of member 50 and apparatus 20, should member 50 topple over. The connection for cable 56 maybe provided in base 150. The base 150 may also contain a battery pack if necessary or desirable for the operation of the remote tactile feedback system. Base 90 may also include a heat sink 152 having fins, as shown in FIG. 5 to reduce any heat build up from actuator 104 or similar components in member 50.

In the alternative, a holster maybe provided on the medical apparatus, such as the ventilator, in which member 50 is placed when not in use.

Figure 6:
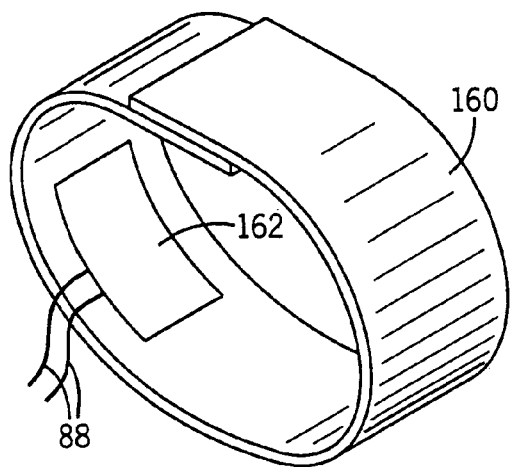
FIG. 6 shows another embodiment of elements for providing a tactile feedback sensation.

While the remote tactile feedback system of the present invention has been shown in an embodiment in which member 50 is placed in the hand of a user, the system is not so limited. For example, member 50 could be designed to be placed on the wrist of a user as shown in FIG. 6 at 160 with a force supplying means 162, such as actuator 104-armature 106, applying pressure to the wrist of the user.

Figure 7:
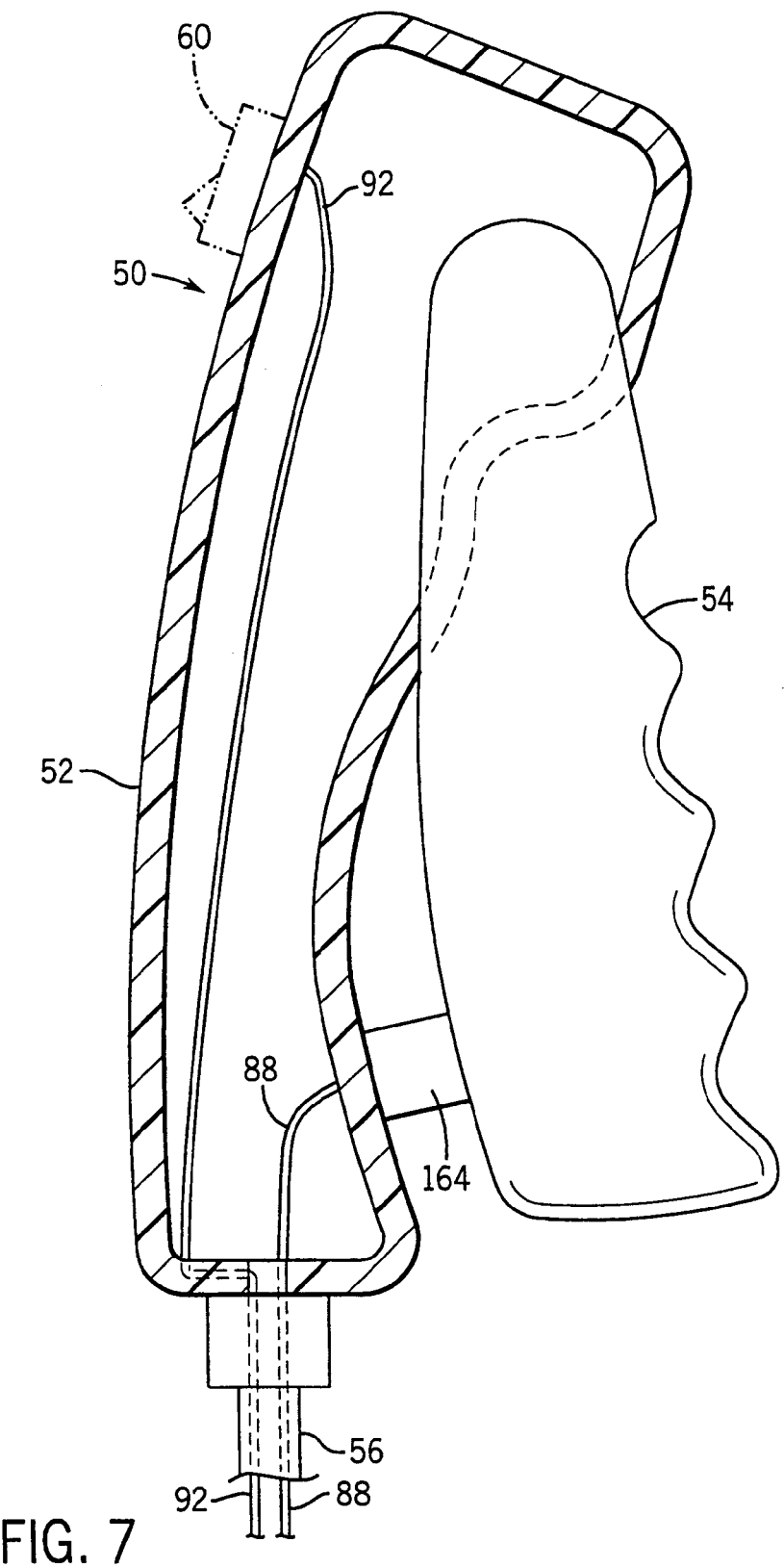
FIG. 7 shows a further modification of the manual element to include a pressure operated element.

Member 50 of the present invention has been shown in an embodiment in which the tactile feedback aspects and the control aspects are provided in a single device, such as member 50. However, it will be appreciated that tactile feedback generator and the control member maybe physically separate from each other. For example, member 50 providing the tactile feedback may be held in the hand of an operator while the control signal generator may comprise a foot, voice, or eye operated device. For example, the control signal generator may comprise a foot actuated switch or potentiometer. Further, while the system has been described above showing control signal generator 94 as having a displaceable element 164, such as trigger 54, the control signal generator may comprise a pressure operated element, such as a piezoelectric element 164 shown in FIG. 7, that senses force applied by the hand, fingers, or foot of the user.

Figure 8:
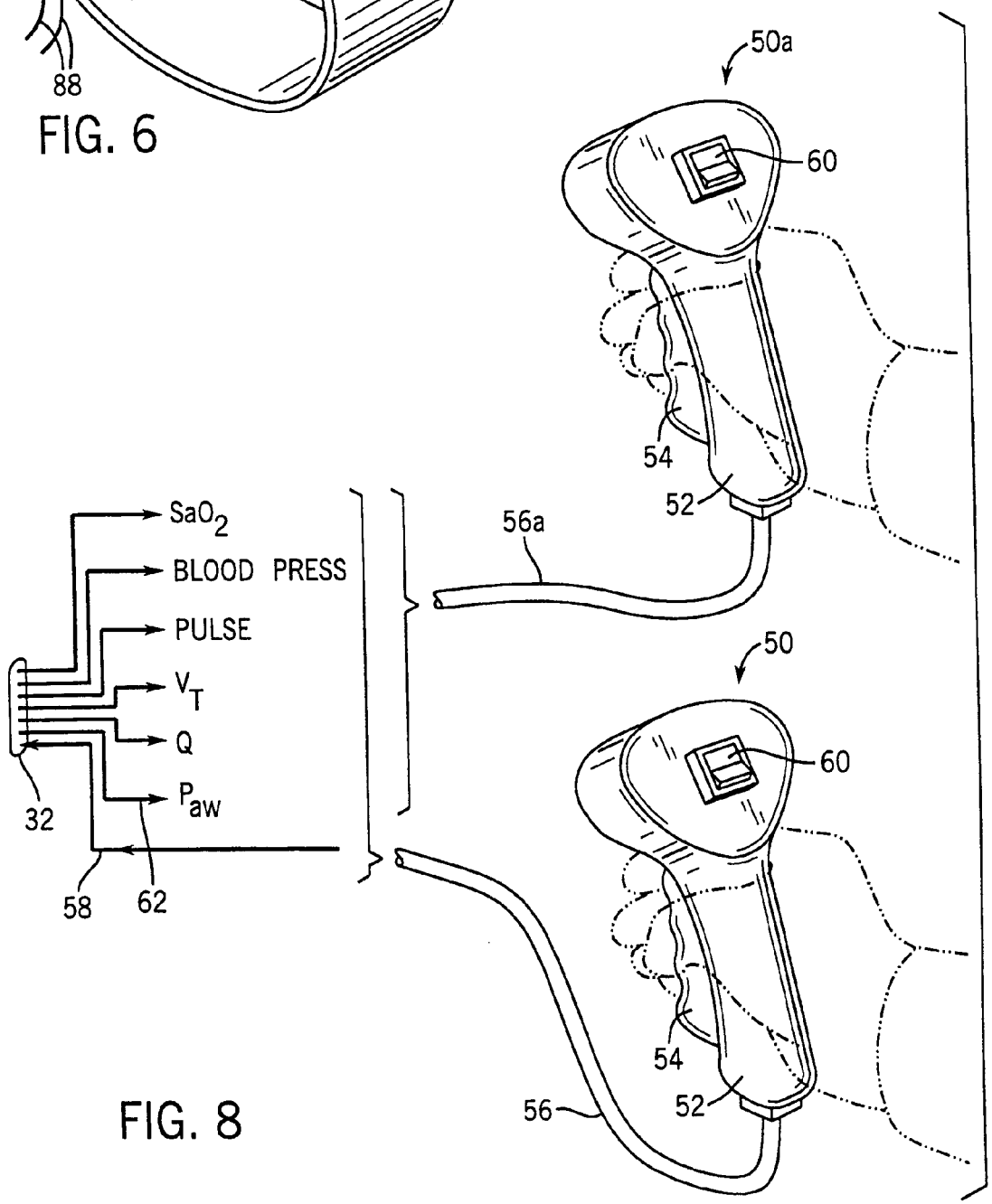
FIG. 8 shows an embodiment of the system having a plurality of manual members.

FIG. 8 shows the system of the present invention with an additional manual member 50a. Member 50a is generally in parallel with member 50 as by a connection to apparatus 20 in cable 56a, as shown in FIG. 8, or to member 50 itself. Such an arrangement may be used in a teaching setting. For example, an instructor may manipulate member 50 and a student holding member 50a will be able to also experience the tactile feedback resulting from the operation of the medical apparatus. Or, the student may operate member 50 and the instructor can monitor his or her actions with member 50a.

Figure 10:
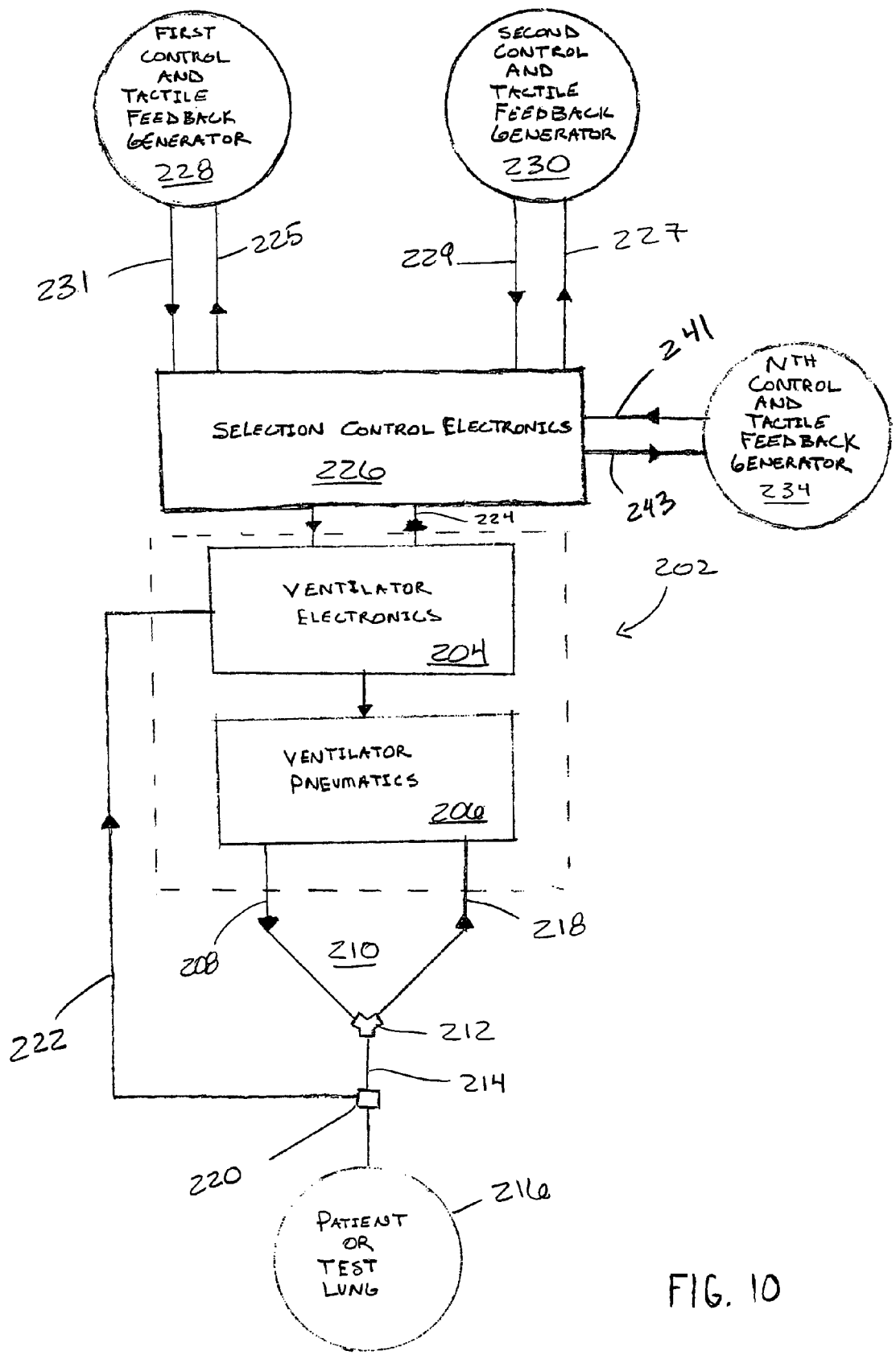
FIG. 10 shows a schematic diagram of a system for monitoring control signals provided to a medical apparatus, such as a ventilator.

FIG. 10 shows a schematic diagram of a system for monitoring control signals provided to a medical apparatus based upon tactile feedback from the apparatus. In the embodiment shown, a ventilator 202 includes electronic circuitry 204 that operates ventilator pneumatic circuitry 206. Pneumatic circuitry 206 comprises a source of pressurized gas that provides breathing gases in inspiratory limb 208 of a patient breathing circuit 210. Pneumatic circuitry 206 may provide breathing gases directly to the lungs of a patient, as in a typical critical care application. Alternatively, a driving gas provided by pneumatic circuitry 206 may compress a bellows (not shown) containing the breathing gases which, in turn, supplies the gases to the patient 216, as in typical anesthesia application. The breathing gases pass through Y-connector 212 to a patient limb 214 for supply to the patient 216. The breathing gases are returned to the ventilator 202 in expiratory limb 218. In the embodiment shown in FIG. 10, a pressure sensor 220 provides an airway pressure $P_{aw}$ signal in conductor 222 to ventilator control electronic circuitry 204. The signal in conductor 222 is proportional to the pressure in patient limb 214 leading to the lungs of the patient 216. Ventilator control electronic circuitry 204 may include a monitor that provides a numeric or graphic display of the patient airway pressure, as well as other patient or apparatus parameters. The signal from the airway pressure sensor 220 is also provided in conductor 224 to selection control electronics 226.

Selection control electronics 226 communicate with a first control and tactile feedback generator 228 and a second control and tactile feedback generator 230. More specifically, selection control electronics 226 are arranged to receive the signal from the airway pressure sensor 220 via ventilator electronics 204 and conductor 224, and transfer the signal to the first control and tactile feedback generator 228 via conductor 225 and to the second control and tactile feedback generator 230 via conductor 227. The selection control electronics 226 is also arranged to receive control signals from the first control and tactile feedback generator 228 via conductor 231 and transfer the signals to the ventilator 202 for carrying out an operation of the ventilator.

In one embodiment, the selection control electronics 226 is also arranged to receive control signals from the second control and tactile feedback generator 230 via conductor 229 and transfer the signals to the ventilator 202 for carrying out an operation of the ventilator.

The control signals from the first and second control and feedback generators 228, 230 are provided to the ventilator electronics 204 to control operation of the ventilator 202. In addition, the control signal from the first control and tactile feedback generator 228 is communicated to the second control and tactile feedback generator 230. In one embodiment, control signals from the second control and tactile feedback generator 230 are provided to the first control and tactile feedback generator 228.

It is also recognized that a plurality of control and tactile feedback generators 234 may be placed in communication with the selection control electronics 226. In this arrangement, the selection control electronics 226 is arranged to receive control signals from any one of the plurality of control and tactile feedback generators 234.

The selection control electronics 226 may be physically integrated with the ventilator electronics 204. Alternately, selection control electronics may be part of one or more of the control and tactile feedback generators, or exist as one or more separate control units. It is further recognized that the conductors 225, 227, 229, 231, 241, 243 may comprise a wireless link or a hardwire extension.

The selection control electronics 226 can be designed to operate in one or more modes. For example, in one mode, control signals from the first control and tactile feedback generator 228 are communicated to the second control and tactile feedback generator 230. In this arrangement, the second control and tactile feedback generator 230 and the plurality of control and tactile feedback generators 234 do not have control over the operation of the ventilator 202, but rather are allowed to monitor the control signals sent by the first control and tactile feedback generator 230. In an alternate mode, control signals from the second control and tactile feedback generator 230 (or a selected one of the plurality of control and feedback generators 234) are communicated to the first control and tactile feedback generator 230. In this mode, the second control and tactile feedback generator 230 is capable of controlling the operation of the ventilator 202.

In one embodiment, selection control electronics 226 provide the first individual with the ability to select the mode according to which the system operates. For example, the experienced caregiver can select the second control and feedback generator 230, or one of the plurality of control and feedback generators 234 to provide control signals to the apparatus 202. Alternately, the experienced caregiver can prevent control by the second control and tactile feedback generator 230 and the plurality of control and feedback generators 234 and instead designate the first control and feedback generator 228 as the sole controller.

Selection control electronics 226 are preferably programmable with a response signature relating to a specific lung disease, for example, asthma, cystic fibrosis, etc. Accordingly, a caregiver is able to select the signature relating to a particular disease, which is then applied to the feedback generators 228, 230, respectively.

The embodiments described above can be employed in a teaching or clinical setting to significantly reduce the training time necessary to educate clinicians and staff regarding the operation of a medical apparatus, such as the ventilator shown in FIG. 10. In addition, in many applications, students can learn how to operate the apparatus to treat a wide variety of diseases, including less common diseases by programming the selection control electronics 226 to provide specific feedback representative of the particular disease. In the embodiment shown, the first and second control and tactile feedback generators 228, 230 are linked by the selection control electronics 226 such that interactive tactile feedback and control signals provided to and received from the first control and tactile feedback generator 228 (which may be operated by the experienced clinician) are reflected in the second control and tactile feedback generator 230 (which may be operated by the student). Thus, it will be recognized by those skilled in the art that the student is provided with instantaneous feedback regarding real-time actions and reactions for the medical apparatus and the specific patient ailment in the clinical setting.

A further advantage of the system shown in FIG. 10 is that the second control and tactile feedback generator 230, operated by a student, may also communicate control signals to the apparatus, which control signals can be reflected in the first control and tactile feedback generator 228, operated by the experienced caregiver. In this manner, the experienced caregiver can monitor the student's ability to control the apparatus and adapt to the various patient conditions that are exhibited via the tactile feedback.

In one embodiment, the first and second control and tactile feedback generators comprise members 50 such as those illustrated in FIGS. 1-9. In this arrangement, feedback is provided to both the first and second control and tactile feedback generators 228, 230 via a trigger 54. The experienced clinician grasps the first control and tactile feedback generator 228 by the trigger 54 and squeezes the trigger 54 to send a control signal to the apparatus. The gripping motion on the trigger 54 is mirrored in the trigger 54 on the second control and tactile feedback generator 230, held by the student. In this manner, the student is able to monitor, sense and/or feel the control actions provided by the experienced clinician to control the apparatus on actual patients.

In another embodiment, the second control and tactile feedback generator comprises a member 50 such as the one illustrated in FIG. 5, wherein the member 50 has a display 130. In this arrangement, control signals sent by the first control and tactile feedback generator 228 are indicated on the display 130 of the second control and tactile feedback generator 230. This arrangement allows the second individual to visually monitor the control signals sent by the first individual. Accordingly, a student can monitor the control actions of an experienced clinician, or the experienced clinician can monitor signals of the student. It will be recognized by those skilled in the art that the display 130 and member 50 do not have to be physically integrated, but instead may be separate apparatus.

Figure 11:
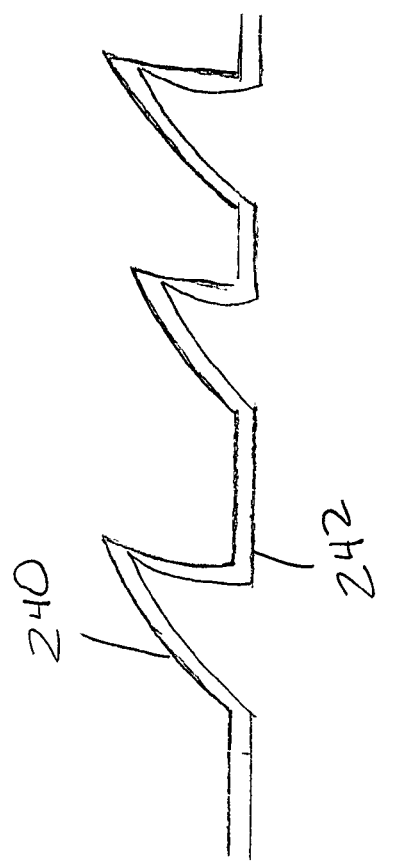
FIG. 11 is an example of a display for displaying control signals provided to a ventilator.

In this arrangement, it is also possible for the student to attempt to mimic the control actions of the experienced clinician. Referring to FIG. 11, the display 130 may indicate the control signals provided by the experienced clinician as a first waveform 240 on an airway pressure vs. time graph. The display 130 could further indicate the control signals provided by the student as a second waveform 242 on the graph. The student can thus visually monitor the first waveform 240 and attempt to mimic the control actions of the experienced clinician by attempting to align the second waveform 242 with the first waveform 240.

Those skilled in the art will recognize that the member 50 could further, or alternatively, provide audio signals indicative of the control signals to allow the first and/or second individuals to monitor the control signals provided by the other.

A further advantage of the system shown in FIG. 10 is that the teacher and students are able to be distant from the apparatus and patient and move about the apparatus and patient to a desired location. The remote nature of the first and second tactile feedback generators 228, 230 provides a large number of individuals to simultaneously monitor the control actions provided by the experienced clinician. The system and method is thus applicable in both the hospital and classroom settings.

The interactive feedback provided to the first and second control and tactile feedback generators 228, 230 does not necessarily have to be associated with an actual patient. In contrast, the apparatus may be connected to a test lung 216 which is designed to simulate the breathing activity of an actual patient.

It is recognized that other equivalents, alternatives, and modifications aside from those expressly stated, are possible and within the scope of the appended claims.

What is claimed is:

1. A system for monitoring control signals provided to a medical apparatus based upon tactile feedback from the apparatus, the system employing a monitoring signal indicative of a parameter relating to the apparatus or to a condition of a patient associated with the apparatus, the system comprising:
   a first feedback device in communication with the apparatus and arranged to provide tactile feedback to a first individual based upon the monitoring signal;
   a first controller actuatable by the first individual to provide a control signal to the apparatus for carrying out a control action in the apparatus;
   the first feedback device and first controller in communication with the apparatus such that the first individual can be distant from the apparatus and patient and move about the apparatus and patient to a desired location;
   a second feedback device in communication with the apparatus and arranged to provide tactile feedback to a second individual based upon the monitoring signal from the apparatus; and
   a second controller in communication with the first controller such that the control signal given by the first individual to the first controller is communicated to the second individual; and
   the second feedback device and second controller in communication with the apparatus such that the second individual can be distant from the apparatus and patient and move about the apparatus and patient to a desired location;
   wherein the second controller is actuatable by the second individual to provide a control signal to the apparatus for carrying out a control action in the apparatus; and
   wherein the second controller is in communication with the first controller such that the control signal given by the second individual to the second controller is reflected in the first controller and communicated to the first individual.

2. A system for monitoring control signals provided to a medical apparatus based upon tactile feedback from the apparatus, the system employing a monitoring signal indicative of a parameter relating to the apparatus or to a condition of a patient associated with the apparatus, the system comprising:
   a first feedback device in communication with the apparatus and arranged to provide tactile feedback to a first individual based upon the monitoring signal;
   a first controller actuatable by the first individual to provide a control signal to the apparatus for carrying out a control action in the apparatus;
   the first feedback device and first controller in communication with the apparatus such that the first individual can be distant from the apparatus and patient and move about the apparatus and patient to a desired location;
   a second feedback device in communication with the apparatus and arranged to provide tactile feedback to a second individual based upon the monitoring signal from the apparatus; and
   a second controller in communication with the first controller such that the control signal given by the first individual to the first controller is communicated to the second individual; and
   the second feedback device and second controller in communication with the apparatus such that the second individual can be distant from the apparatus and patient and move about the apparatus and patient to a desired location;
   wherein the first controller is suitable for being placed in the hand of the first individual and wherein the first controller has a trigger member connected to a signal generating element for providing the control signal;
   wherein the second controller is suitable for being placed in the hand of the second individual and has a trigger member connected to a signal generating element for providing a control signal to the apparatus; and
   wherein movements of the trigger on the first controller cause corresponding movement of the trigger on the second controller.

3. A system for monitoring control signals provided to a medical apparatus based upon tactile feedback from the apparatus, the system employing a monitoring signal indicative of a parameter relating to the apparatus or to a condition of a patient associated with the apparatus, the system comprising:
   a first feedback device in communication with the apparatus and arranged to provide tactile feedback to a first individual based upon the monitoring signal;
   a first controller actuatable by the first individual to provide a control signal to the apparatus for carrying out a control action in the apparatus;
   the first feedback device and first controller in communication with the apparatus such that the first individual can be distant from the apparatus and patient and move about the apparatus and patient to a desired location;
   a second feedback device in communication with the apparatus and arranged to provide tactile feedback to a second individual based upon the monitoring signal from the apparatus; and a second controller in communication with the first controller such that the control signal given by the first individual to the first controller is communicated to the second individual;

the second feedback device and second controller in communication with the apparatus such that the second individual can be distant from the apparatus and patient and move about the apparatus and patient to a desired location; and wherein the second controller is actuatable by the second individual to provide a control signal to the apparatus for carrying out a control action in the apparatus; and further comprising selection control electronics for selecting which one of the first or second controllers to control the apparatus.

4. A system for monitoring control signals provided to a medical apparatus based upon tactile feedback from the apparatus, the system employing a monitoring signal indicative of a parameter relating to the apparatus or to a condition of a patient associated with the apparatus, the system comprising:

a first feedback device in communication with the apparatus and arranged to provide tactile feedback to a first individual based upon the monitoring signal;

a first controller actuatable by the first individual to provide a control signal to the apparatus for carrying out a control action in the apparatus;

the first feedback device and first controller in communication with the apparatus such that the first individual can be distant from the apparatus and patient and move about the apparatus and patient to a desired location;

a second feedback device in communication with the apparatus and arranged to provide tactile feedback to a second individual based upon the monitoring signal from the apparatus; and a second controller in communication with the first controller such that the control signal given by the first individual to the first controller is communicated to the second individual;

the second feedback device and second controller in communication with the apparatus such that the second individual can be distant from the apparatus and patient and move about the apparatus and patient to a desired location;

wherein the control signal given by the first individual to the first controller is communicated to the second individual via tactile feedback.

5. A combined remote control and tactile feedback system and respiratory ventilator, the feedback system employing a signal indicative of a parameter relating to the respiratory ventilator or to a patient associated with the respiratory ventilator and comprising:

a first member allowing a first user to move about the respiratory ventilator or patient while controlling the respiratory ventilator and receiving a tactile feedback of a parameter, said first member comprising:

a first control device actuatable by the first user to provide a control signal for carrying out a control action in the respiratory ventilator;

a first feedback device suitable for being placed in contact with a selected body portion of the first user for generating a tactile sensation that can be experienced by the first user; and a first communication link placing the first control device and the first feedback device in communication with the respiratory ventilator in a manner that allows the first user to move about the respiratory ventilator and patient and to be at a distance from the respiratory ventilator, said first communication link communicating the control signal to the respiratory ventilator to control the respiratory ventilator, said communication link communicating the signal indicative of the parameter to said first feedback device, said first feedback device employing said parameter signal to generate a tactile sensation to the body of the first user corresponding to the parameter;

a second member providing a tactile feedback of the parameter to a second user remote from the respiratory ventilator, said second member comprising:

a second feedback device suitable for being placed in contact with a selected body portion of the second user for generating a tactile sensation that can be experienced by the second user; and a second communication link placing the second feedback device in communication with the respiratory ventilator in a manner that allows the second user, when in contact with said second feedback device, to be distant from the respiratory ventilator and to move about the respiratory ventilator and patient to a desired location, said second communication link communicating the signal indicative of the parameter to said second feedback device, said second feedback device employing said parameter signal to generate a tactile sensation to the body of the second user corresponding to the parameter, wherein the arrangement is such that the second user is able to experience the tactile feedback resulting from the operation of the respiratory ventilator by the first user.

6. The combined system and respiratory ventilator of claim 5, wherein the arrangement is such that the second user can monitor the first user's actions.

7. The combined system and respiratory ventilator of claim 5, wherein at least one of said first and second feedback devices includes an actuator for generating a force on the selected body portion of the user, said actuator comprising one of an electrical and a fluid operated actuator.

8. The combined system and respiratory ventilator of claim 5 for controlling the flow of breathing gases to a patient wherein said first control device is further defined as including means to carry out a control action of providing a breathing gas flow magnitude to the patient that is proportional to a rate of change of a variable magnitude control member signal.

9. The combined system and respiratory ventilator of claim 5, wherein said first control device includes a displaceable, signal generating element for providing the signal.

10. The combined system and respiratory ventilator of claim 9, wherein said first control device is suitable for being placed in the hand of an operator and has a trigger member connected to a signal generating element for providing the signal.

11. The combined system and respiratory ventilator of claim 5, wherein said first control device and said first feedback device comprise a common element, said common element optionally being further defined as suitable for being placed in contact with the hand of the user and including a trigger for being placed in contact with the fingers of the first user, said first feedback device including an actuator for said trigger operable by said parameter signal.

12. The combined system and respiratory ventilator of claim 5, further including a display for displaying information for a user.

13. The combined system and respiratory ventilator of claim 5, wherein said first communication link and said second communication link each comprise a cable or a telemetry link.

14. The combined system and respiratory ventilator of claim 5 for controlling the flow or pressure of breathing gases to a patient and wherein said first control device is further defined as providing a breathing gas flow control signal or a breathing gas pressure control signal.

15. The combined system and respiratory ventilator of claim 5, wherein said system generates a tactile sensation of a parameter comprising one of patient airway pressure, patient breathing gas flow, patient tidal volume, patient pulse rate, patient blood pressure, and patient arterial blood oxygen saturation.

16. The combined system and respiratory ventilator of claim 5, wherein said communication means communicates a plurality of signals indicative of parameters to said first and second feedback devices and wherein said feedback generates tactile sensations to the bodies of the first and second users incorporating a plurality of parameter signals.

17. A combined remote control and tactile feedback system and respiratory ventilator, the feedback system employing a signal indicative of a parameter relating to the respiratory ventilator or to a patient associated with the respiratory ventilator and comprising:
   a first member allowing a first user to move about the respiratory ventilator or patient while controlling the respiratory ventilator and receiving a tactile feedback of a parameter, said first member comprising:
   a first control device actuatable by the first user to provide a control signal for carrying out a control action in the respiratory ventilator;
   a first feedback device suitable for being placed in contact with a selected body portion of the first user for generating a tactile sensation that can be experienced by the first user; and
   a first communication link placing the first control device and the first feedback device in communication with the respiratory ventilator in a manner that allows the first user to move about the respiratory ventilator and patient and to be at a distance from the respiratory ventilator, said first communication link communicating the control signal to the respiratory ventilator to control the respiratory ventilator, said communication link communicating the signal indicative of the parameter to said first feedback device,
   said first feedback device employing said parameter signal to generate a tactile sensation to the body of the first user corresponding to the parameter;
   a second member providing a tactile feedback of the parameter to a second user remote from the respiratory ventilator, said second member comprising:
   a second feedback device suitable for being placed in contact with a selected body portion of the second user for generating a tactile sensation that can be experienced by the second user;
   a second communication link placing the second feedback device in communication with the respiratory ventilator in a manner that allows the second user, when in contact with said second feedback device, to be distant from the respiratory ventilator and to move about the respiratory ventilator and patient to a desired location, said second communication link communicating the signal indicative of the parameter to said second feedback device, said second feedback device employing said parameter signal to generate a tactile sensation to the body of the second user corresponding to the parameter; and
   means in said respiratory ventilator for adjusting the sensitivity between the control signal and the resulting control action in the respiratory ventilator or between the parameter signal and the resulting tactile signal generation.

18. The combined system and respiratory ventilator of claim 17, wherein at least one of said signals has a magnitude range and wherein said adjusting means alters the sensitivity over the magnitude range of the signal.

19. A combined remote control and tactile feedback system and respiratory ventilator, the feedback system employing a signal indicative of a parameter relating to the respiratory ventilator or to a patient associated with the respiratory ventilator and comprising:
   a first member allowing a first user to move about the respiratory ventilator or patient while controlling the respiratory ventilator and receiving a tactile feedback of a parameter, said first member comprising:
   a first control device actuatable by the first user to provide a control signal for carrying out a control action in the respiratory ventilator;
   a first feedback device suitable for being placed in contact with a selected body portion of the first user for generating a tactile sensation that can be experienced by the first user; and
   a first communication link placing the first control device and the first feedback device in communication with the respiratory ventilator in a manner that allows the first user to move about the respiratory ventilator and patient and to be at a distance from the respiratory ventilator, said first communication link communicating the control signal to the respiratory ventilator to control the respiratory ventilator, said communication link communicating the signal indicative of the parameter to said first feedback device,
   said first feedback device employing said parameter signal to generate a tactile sensation to the body of the first user corresponding to the parameter;
   a second member providing a tactile feedback of the parameter to a second user remote from the respiratory ventilator, said second member comprising:
   a second feedback device suitable for being placed in contact with a selected body portion of the second user for generating a tactile sensation that can be experienced by the second user; and
   a second communication link placing the second feedback device in communication with the respiratory ventilator in a manner that allows the second user, when in contact with said second feedback device, to be distant from the respiratory ventilator and to move about the respiratory ventilator and patient to a desired location, said second communication link communicating the signal indicative of the parameter to said second feedback device,
   said second feedback device employing said parameter signal to generate a tactile sensation to the body of the second user corresponding to the parameter,
   means in communication with said first communication link for establishing desired properties of linearity-non linearity between the control signal and the resulting control action in the ventilator or between the parameter signal and the resulting tactile sensation generation.

20. The combined system and respiratory ventilator of claim 19, wherein at least one of said signals has a magnitude range and wherein said linearity-non linearity establishing means alters the linearity-non linearity properties over the magnitude range of the signal.

* * * * *